U S008557274B2

(12) United States Patent  
Hamaker et al.

(10) Patent No.: US 8,557,274 B2  
(45) Date of Patent: Oct. 15, 2013

(54) SLOWLY DIGESTING STARCH AND FERMENTABLE FIBER

(75) Inventors: Bruce R. Hamaker, West Lafayette, IN (US); Mahesh Venktachalam, West Lafayette, IN (US); Genyi Zhang, West Lafayette, IN (US); Ali Keshavarzian, Evanston, IL (US); Devin J. Rose, West Lafayette, IN (US)

(73) Assignees: Purdue Research Foundation, West Layayette, IN (US); Rush University Medical Center, Chicago, IL (US)

( * ) Notice: Subject to any disclaimer, the term of this patent is extended or adjusted under 35 U.S.C. 154(b) by 549 days.

(21) Appl. No.: 11/567,680

(22) Filed: Dec. 6, 2006

(65) Prior Publication Data

US 2007/0196437 A1 Aug. 23, 2007

Related U.S. Application Data

(60) Provisional application No. 60/742,923, filed on Dec. 6, 2005.

(51) Int. Cl.  
*A61K 47/00* (2006.01)

(52) U.S. Cl.  
USPC .............................. 424/439; 514/60; 536/102

(58) Field of Classification Search  
USPC .............................. 424/439; 514/60; 536/102  
See application file for complete search history.

(56) References Cited

U.S. PATENT DOCUMENTS

| | | | |
|---|---|---|---|
| 2,517,595 A | 8/1950 | Owens et al. | |
| 2,611,708 A | 9/1952 | Owens et al. | |
| 2,703,286 A | 3/1955 | Eppell | |
| 3,729,380 A | 3/1973 | Sugimoto et al. | |
| 4,139,505 A | 2/1979 | Rogols et al. | |
| 4,192,900 A | 3/1980 | Cheng | |
| 4,465,702 A | 8/1984 | Eastman et al. | |
| 4,663,177 A | 5/1987 | Weaver et al. | |
| 4,911,952 A | 3/1990 | Doane et al. | |
| 5,037,929 A | 8/1991 | Rajagopalan et al. | |
| 5,051,271 A | 9/1991 | Iyengar et al. | |
| 5,131,953 A | 7/1992 | Kasica et al. | |
| 5,149,799 A | 9/1992 | Rubens | |
| 5,268,367 A | 12/1993 | Miwa et al. | |
| 5,294,455 A | 3/1994 | O'Brien et al. | |
| 5,360,614 A | 11/1994 | Fox et al. | |
| 5,387,426 A | 2/1995 | Harris et al. | |
| 5,417,982 A | 5/1995 | Modi | |
| 5,536,156 A | 7/1996 | Fox et al. | |
| 5,545,410 A | 8/1996 | Fox et al. | |
| 5,562,937 A | 10/1996 | Senkeleski et al. | |
| 5,599,569 A | 2/1997 | Chiu et al. | |
| 5,612,202 A | 3/1997 | Brumm et al. | |
| 5,795,606 A | 8/1998 | Lapré et al. | |
| 5,849,090 A | 12/1998 | Haralampu et al. | |
| 5,855,946 A | 1/1999 | Seib et al. | |
| 5,962,047 A | 10/1999 | Gross et al. | |
| 5,972,399 A * | 10/1999 | Lapre et al. | 426/302 |
| 6,043,229 A | 3/2000 | Kettlitz et al. | |
| 6,090,594 A | 7/2000 | Kettlitz et al. | |
| 6,238,705 B1 * | 5/2001 | Liu et al. | 424/501 |
| 6,248,375 B1 | 6/2001 | Gilles et al. | |
| 6,316,427 B1 | 11/2001 | Axelson et al. | |
| 6,322,841 B1 | 11/2001 | Jackson et al. | |
| 6,623,943 B2 | 9/2003 | Schmiedel et al. | |
| 6,649,191 B1 * | 11/2003 | Tester et al. | 424/488 |
| 6,664,389 B1 | 12/2003 | Shi et al. | |
| 6,720,312 B2 | 4/2004 | Chawan | |
| 6,815,436 B2 | 11/2004 | Hansson et al. | |
| 6,890,571 B2 | 5/2005 | Shi et al. | |
| 6,929,817 B2 | 8/2005 | Shi et al. | |
| 7,053,066 B2 | 5/2006 | Chawan | |
| 7,081,261 B2 | 7/2006 | Shi et al. | |
| 2001/0053359 A1 | 12/2001 | Watts et al. | |
| 2003/0094172 A1 | 5/2003 | Bengs et al. | |
| 2003/0161876 A1 | 8/2003 | Hansson et al. | |
| 2003/0215562 A1 | 11/2003 | Shi et al. | |
| 2003/0219520 A1 | 11/2003 | Shi et al. | |
| 2004/0013789 A1 | 1/2004 | Klukowski | |
| 2005/0227911 A1 | 10/2005 | Goldshtein et al. | |

(Continued)

FOREIGN PATENT DOCUMENTS

| | | |
|---|---|---|
| EP | 0 564 893 | 10/1993 |
| EP | 0 688 872 | 12/1995 |

(Continued)

OTHER PUBLICATIONS

JP-406276961—Abstract. The last two pages of the attached Japanese patent include the English abstract of the patent.*

(Continued)

*Primary Examiner* — D. Lawrence Tarazano  
*Assistant Examiner* — Hamid R Badr  
(74) *Attorney, Agent, or Firm* — Purdue Research Foundation; Elizabeth A. Hart-Wells; Hamid R. Piroozi (57) ABSTRACT

Compositions which provide slowly digestible starch and a source of fermentable dietary fiber. Microparticles in which starch is entrapped in a crosslinked matrix to provide dietary benefit. Such microparticles are used to deliver glucose to targeted regions in the small intestine for beneficial physiological effects, and fermentable dietary fiber to the colon to improve colon health and to treat diseases of the colon. Microparticles can be employed to selectively deliver fermentable dietary fiber to targeted portions of the colon. A method for making the microparticles is provided as well as methods for using the microparticles for controlled digestion of starch on ingestion in the small intestine and methods for using the microparticles to deliver dietary fiber. The microparticles with entrapped starch provide a low glycemic index and extended glucose release in food products and food ingredients. The microparticles with entrapped starch can, in particular, be used as an ingredient in foods that are to be cooked.

17 Claims, 5 Drawing Sheets

(56) References Cited

U.S. PATENT DOCUMENTS

| | | | |
|---|---|---|---|
| 2006/0127453 A1* | 6/2006 | Harel | 424/442 |
| 2007/0082109 A1 | 4/2007 | Muller et al. | |
| 2007/0134392 A1 | 6/2007 | Muller et al. | |

FOREIGN PATENT DOCUMENTS

| | | | |
|---|---|---|---|
| EP | 0749697 | | 12/1996 |
| JP | 2002114605 | | 4/2002 |
| WO | WO 00/32064 | * | 6/2000 |
| WO | WO 2004/066955 | | 8/2004 |
| WO | WO 2005/044284 | | 5/2005 |
| WO | WO 2005/048980 | | 6/2005 |
| WO | WO 2005/058973 | | 6/2005 |

OTHER PUBLICATIONS

American Association of Cereal Chemists International (Jan. 10, 2001) *Report of the Dietary Fiber Definition Committee to the Board of Directors of AACC* http://www.aaccnet.org/grainbin/definitiondietaryfiber.asp.

Becker et al. (2001) "Calcium Alginate Gel: A Biocompatible and Mechanically Stable Polymer for Endovascular Embolization," *J. Biomed. Mater. Res.* 54:76-86.

Berger et al. (2004) "Structure and Interactions in Covalently and Ionically Crosslinked Chitosan Hydrogels for Biomedical Applications," *Eur. J. Pharm. Biopharm.* 57:19-34.

Cairns et al. (1996) "Physicochemical Studies on Resistant Starch IN Vitro and in Vivo," *J. Cereal Science* 23:265-275.

Cui et al. (1997) "The Effect of Retrogradation on Enzyme Susceptibility of Sago Starch," *Carbohydrate Polymers* 32:65-72.

Eller et al. (Oct. 1971) "Anaerobic Roll Tube Media for Nonselective Enumeration and Isolation of Bacteria in Human Feces," *Appl. Microbiol.* 22(4):522-529.

Englyst et al. (1992) "Classification and Measurement of Nutritionally Important Starch Fractions," *Eur. J. Clin. Nut.* 46(Supp. 2):533-550.

Englyst et al. (1996) "Measurement of Rapidly Available Glucose (RAG) in Plant Foods: A Potential in Vitro Predictor of the Glycaemic Response," *Br. J. Nutr.* 75:327-337.

Esposito et al. (2001) "Pectin-Based Microspheres—A Preformulatory Study," *Ann. NY Acad. Sci.* 944:160-179.

Fao Food and Nutrition Paper 66 (1997) "The Role of the Glycemic Index in Food Choice," in; *Carbohydrates in Human Nutrition*, Ch. 4, The role of the Glycemic Index in Food Choice, Report from Apr. 14-18, pp. 25-30.

Fredriksson et al. (2000) "Studies on Alpha-Amylase Degradation of Retrograded Starch Gels from Waxy Maize and High Amylopectin Potato," *Carbohydrate Polymers* 43:81-87.

Guraya et al. (2001) "Effect of Enzyme Concentration and Storage Temperature on the Formation of Slowly Digestible Starch from Cooked Debranched Rice Starch," *Starch/Starke* 53:131-139.

Han et al. (2006) "Development of a Low Glycemic Maize Starch: Preparation and Characterization," *Biomacromolecules* 7:1162-1168.

International Search Report, Corresponding to International Application No. PCT/US04/02566, Mailed Mar. 10, 2006.

Kailasapath, K. (2006) "Evaluation of Alginate-Starch Polymers for Preparation of Enzyme Microcapsules," *Int. J. Food Eng.* 2(2).

Lebet et al. (1998) "Digestion Procedure Using Mammalian Enzymes to Obtain Substrates for in Vitro Fermentation Studies," *Lebensmittel Wissenschaft and Technologie* 31:509-515.

MacDougal et al. (1996) "Calcium Gelation of Pectic Polysaccharides Isolated from Unripe Tomato Fruit," *Carbohydrate Res.* 923:235-249.

Obanni et al. (1995) "Identification of Starch from Various Maize Endosperm Mutants Via Ghost Structures," *Cereal Chem.* 72:436-442.

Playne (1985) "Determination of Ethanol, Volatile Fatty Acids, Lactic Acid and Succinic Acids in Fermentation Liquids by Gas Chromatography," *J. Sci. Food Agric.* 36:638-644.

Sievert et al. (1989) "Enzyme-Resistant Starch. I Characterization and Evaluation by Enzymatic Thermoanalytical and Microscopic Methods," *Cereal Chemistry* 64:342-347.

Tejashree et al. (2003) "Starch-Based Spherical Aggregates: Screening of Small Granule Sized Starches for Entrapment of a Model Flavouring Compound, Vanillin," *Carb. Polym.* 53(1):45-51.

Wachters-Hagedoorn et al. (Jun. 2006) "The Rate of Intestinal Glucose Absorption Is Correlated with Plasma Glucose-Dependent Insulinotropic Polypeptide Concentrations in Healthy Men," *J. Nutr.* 136(6):1511-1516.

Wolever et al. (2005) "Glycaemic Index Methodology," *Nut. Res. Rev.* 18:145-171.

McHugh, D, (1987) "Production, Properties and Uses of Alginates," in *Production and Utilization of Products from Commercial Seaweeds*, FAO Fisheries Technical Paper Series, produced by Food and Agriculture Organization of the United Nations (Fisheries and Aquacuiture Department), downloaded from http://www.fao.org/docrep/X5822E/x5822E00.htm) May 2012.

Kaur A., Rose, D. J., Rumpagaporn, P., Patterson, J.A., Hamaker, B.R. (2011) In Vitro Batch Fecal Fermentation Comparison of Gas and Short-Chain Fatty Acid Production Using "Slowly Fermentable" Dietary Fibers J. Food Science, vol. 76(5):H137-H142.

* cited by examiner

SLOWLY DIGESTING STARCH AND FERMENTABLE FIBER

CROSSREFERENCE TO RELATED APPLICATIONS

This application claims priority from U.S. provisional patent application Ser. No. 60/742,923 filed Dec. 6, 2005 which is incorporated in its entirety by reference herein.

STATEMENT REGARDING U.S. GOVERNMENT FUNDING

This work was funded with U.S. government funding through the USDA/CSREES grant 2005-34328-16024. The United States government has certain rights in this invention.

BACKGROUND OF THE INVENTION

Starch, being the principal component in most staple foods such as cereals and tubers, is the major food carbohydrate contributing to postprandial glycemia. Digestibility of starch is directly associated with glycemic/insulinemic response and the occurrence of glucose metabolism-related health conditions like diabetes and pre-diabetes, cardiovascular disease, and obesity. Therefore, the glycemic index (GI) or glycemic response of starch in foods is increasingly becoming an important factor for human health.

GI is a measure of the rise in blood glucose level that is triggered by consumption of a carbohydrate and relates to the blood glucose profile seen over a period of 2 hours (hr) after consumption of a starch-based or sugar-containing food. GI is typically measured as the area under the blood glucose response curve (AUC) for a given amount of available carbohydrate in a test food (usually 50 g) as compared to the same amount of a reference food (usually glucose or white bread) (Wolever et al., 1991; FAO/WHO, 1997). The higher the GI the greater the blood glucose rise. Typically, a GI of 55 or less is low while a GI of 70 or more is high. Glycemic load (GL), a term related to GI, is a measure, not only GI of a given food, but also considers the amount of carbohydrate in a certain amount (e.g., serving size) of a given food. GL is GI/100 multiplied by the available carbohydrate content of a standard amount of food in grams (i.e. carbohydrates minus fiber). GI and GL of foods consumed may relate to a number of disease and pre-disease conditions such as diabetes and pre-diabetes, cardiovascular disease, cancer, and obesity. GI and GL may also relate to energy expenditure and activity level.

From a nutritional standpoint, starch has been classified into three categories based on in vitro digestion time: rapidly digestible starch (RDS) is converted to glucose in 20 minutes (min), slowly digestible starch (SDS) between 20 and 120 min, and resistant starch (RS) undigested after 120 min (Englyst et al., 1992,1996). Foods with high proportion of RDS have a high GI value based on a correlative relationship between RDS and GI (Englyst et al., 1996). The rapid increase of blood glucose level from RDS triggers the secretion of insulin from pancreas beta-cells to promote glucose uptake by muscle and adipose tissues to maintain blood glucose homeostasis, and, if the increase in postprandial glycemia is pronounced, usually generates a hypoglycemic episode between 1 and 2 hr after consumption of RDS. A long-term fluctuation of postprandial blood glucose and insulin levels will generate high stress on the glucose homeostasis regulation system, which has been directly associated with hyperinsulinemia, insulin resistance, and incidence of Type 2 diabetes.

In contrast, SDS is that portion of starch digested slower than RDS, implying that it is digested throughout the small intestine to provide a slow and prolonged release of glucose over an extended period of time. Such a moderated and controlled release of glucose may place less stress on the blood glucose regulatory system, thereby resulting in health benefits of SDS starches not only in commonly consumed foods, but also in medical applications-foods, drugs, and dietary supplements. Such SDS foods may also provide slow and sustained energy release for athletic performance, improved activity levels (memory and mental performance), and promote increased satiety for weight management.

RS is that portion of starch not digested in the small intestine. RS is, however, digested by colonic microflora amylases, and then fermented to produce short chain fatty acids (SCFAs) (acetic, propionic, and butyric).

Evidence has shown that glycemic response is highly correlated with the amount of RDS in food products, while SDS and RS are associated with hunger satiation and benefits resulted from their effects on a cascade of metabolic consequences including the release of incretin hormones [glucagon-like peptide-1 (GLP) and glucose-dependent insulinotropic polypeptide (GLP)] and slow release of insulin. Thus, starch digestion properties have been implicated in the health problems of diabetes, obesity and cardiovascular disease. Making food products with high amount of slowly digestible starch or resistant starch is currently one of the important targets of food industry.

The importance of dietary fiber in human diet and its numerous physiological functions, as well as role in the prevention and treatment of certain diseases including cardiovascular, diabetes and obesity, and more importantly those related to colon health: inflammatory bowel disease (IBD) and colon cancer, is well recognized. "Dietary fiber is the edible parts of plants or analogous carbohydrates that are resistant to digestion and absorption in the human small intestine with complete or partial fermentation in the large intestine." See: Report of the Dietary Fiber Definition Committee to the Board of Directors of AACC (American Association of Cereal Chemists) International (Jan. 10, 2001). Fiber that is consumed by individuals may include natural fiber from the foods eaten as well as fiber generated from other sources added to a given food (added fiber). Fiber has also be categorized as fermentable and non-fermentable based on the extent of its fermentation in the colon. RS starch is dietary fiber and fermentable fiber under these definitions.

Health benefits are derived from both non-fermentable fiber (among others: increased fecal bulk-affecting fecal output, dilution and increased transit time of carcinogens and toxins in the colon, increased bile salt binding there by influencing cholesterol levels in the blood, and increased digesta viscosity) and fermentable fiber (production of short chain fatty acids that most importantly prevent the growth of harmful bacteria and decrease the inflammatory response). Fiber fermentation produces short chain fatty acids (e.g., acetic, propionic, and butyric acids) that contribute to colon health by increasing blood flow, improving mineral and water absorption by maintenance of low luminal pH. Butyrate has also been shown to have a positive influence on epithelial metabolism, cell cycling, the immune response, and intestinal motility. Two aspects of fermentable fiber that have received attention are preferable production of butyrate, which has promising effects for treatment of colon disorders including irritable bowel disease and colon cancers, and slow fermentation rate so that fermentation occurs in both the proximal part of the colon, and in the distal part of the colon (where most cancer lesions are known to occur). Most fermentable fibers are very rapidly fermented in the proximal part of the colon with very little fermentation in the distal part.

In food science, probiotics are used to deliver living bacterial cells to the gut of humans (and other animals) to adjust the gut ecosystem to improve health or provide health benefits. The use of probiotics is based on the concept that there is a healthy balance of bacteria in the intestinal tracts and that dysbiosis, the disruption of that balance, can result in illness. Probioitcs, for example, are used to restore the balance of gut flora which may be disrupted by antibiotic treatment. Probioites commonly include strains of Lactobacillis and Bifidobacterium which are considered to be beneficial to digestive health. Prebiotics are non-digestible foods which promote the growth of such beneficial bacteria in the gut. Prebiotics include various oligosaccharides, including fructooligosaccharides, inulins, lactilol, lactosucrose, lactulose, and pyrodextrins which in some way stimulate the growth of beneficial gut bacteria.

There is a need in the art for the development of dietary fibers that preferably generate butyrate on fermentation and that are available for fermentation throughout the length of the colon (both proximal and distal). Starch-based dietary fiber offers a distinct advantage because its fermentation produces proportionally more butyrate than traditional dietary fibers. Starch-based dietary fiber can also function as a prebiotic to stimulate the growth of beneficial gut bacteria, including for example Lactobacillis and Bifidobacterum strains.

A starch-based fiber material which exhibits slow fermentation, such that fermentation occurs over the length of the colon, would be of significant interest and benefit in the food and pharmaceutical arts as a food product, food ingredient, nutritional supplement or medicament. Such a fiber material would have additional health benefits generally promoting colon health and more specifically for prevention and/or treatment of diseases of the colon. A starch-based composition which combines low glycemic index with controlled-rate of glucose release with the benefits of fermentable fiber would clearly be of significant interest and benefit as a food product, food ingredient, and nutritional supplement for use by individuals for weight control and maintenance, by those with a predisposition to diabetes (prediabetics), for diabetics and more generally by those wishing to generally maintain healthy nutrition and those wishing to maintain or improve their colonic health. Furthermore, such a starch-based composition would be useful as a prophylactic composition to prevent colon disease, or as a pharmaceutical composition or medicament for treatment of diseases of the colon.

While native starches can be an excellent source of SDS and RS, the slowly digesting property is lost during thermal food processing resulting in RDS and high GI foods. The present invention provides starch-based compositions which are useful as low GI foods, even on cooking, and which provide the benefits of a starch-based fermentable fiber.

Several patents and patent applications report means for overcoming the rapidly digesting characteristics of starch. Some report the use of native starch (U.S. Pat. No. 6,316,427; WO 2005/044284 A1) and treated starches (WO 2005044284, WO 2005058973) for creation of SDS starches. Others report the use of enzymatic modification of starches (U.S. Pat. Nos. 6,890,571 and 6,929,817, W02004066955).

Methods incorporating polysaccharides for encapsulating, coating, or encasing foods have been reported. For example, U.S. Pat. Nos. 2,517,595; 2,611,708; and 2,703,286 report the use of pectin-calcium based films for encasing foods. U.S. Pat. No. 4,192,900 describes the use of a range of starch materials and polymers for preparation of texturized starch products.

U.S. Pat. Nos. 5,360,614 and 5,536,156 report a method for controlling the release of carbohydrates by encapsulation in edible coatings which is said to provide a delayed release of the carbohydrate, thereby making them useful in diabetes and exercise programs calling for sustained energy release.

U.S. Pat. Nos. 5795606 and 5972399 report the use of a cation crosslinked polysaccharide coating to substantially reduce the glycemic response of ready-to-eat, nonfried foods made up of a cooked and hydrated carbohydrate core. The food is reported to be useful for the treatment of diabetes, hypoglycemia, and glycogen storage disease, and for suppressing appetite and assisting the performance of sustained physical activity. The invention also reports on a food preparation consisting of a coated carbohydrate core for cooking in an aqueous medium. The food preparation is described as a crosslinkable polysaccharide coated carbohydrate core that is further crosslinked during cooking of the food in a medium comprising the dissolved cation. The invention also reports to a method of preparing a food, comprising heating the indicated coated core in an aqueous medium comprising crosslinking cations. The heating is done to crosslink the crosslinkable polysaccharide and to cook and to hydrate the core. The carbohydrates reported suitable for the core may include one or more of the following: peptidoglycan, polysaccharide, oligosaccharide, disaccharide, monosaccharide and sugar alcohol. In particular, the carbohydrate may be starch, dextrin, sucrose, mannose, maltose, glucose, fructose, lactitol, xylitol, sorbitol, lactose and mannitol. Most preferably, the carbohydrate includes at least starch. Some examples of the carbohydrate-containing foods included for the core are: rice grains, pasta, breakfast cereal, and vegetables (whole, cubes, dices, slices or chips). Further, the reported core may also be a food ingredient such as a flour granule or granules, or a starch granule or granules. Such food ingredients, i.e., suitable for employment as the core of the invention, include those incorporated into puddings, candy bars, and food bars, and into instant foods such as soups and dessert mixes.

U.S. Pat. No. 6,815,436 reports granulated starch compositions for treatment and/or prevention of dysglucemia. Enzymatic degradation of starch is reported to be controlled in vivo by "minimizing the surface area available to enzymatic action." Starch granules are described as being granulated with a substance resulting in aggregated granules being at least partially encapsulated in the substance. Suitable substances are said to be non-toxic and generally recognized as safe. Suitable substances are said to include "polymers such as gum arabicum, potassium alginate, guar gum, methyl cellulose, ethyl cellulose, liquid oils, liquid and hard fats and waxes, such as paraffin, hydrogenated cottonseed oil, beeswax and carnauba wax." Dysglucaemia is reported to be treated by administering a predetermined amount of starch in the granulated and at least partially encapsulated form. Granulation is reported to delay enzymatic degradation of the starch into reducing sugars, such as glucose. One advantage of the reported composition is stated to be that "practically all of the starch" in the composition is converted to reducing sugars allowing the accurate control of the dose optimized for each patient. Additionally it is stated that the release rate and content of reducing sugars can be accurately controlled and adjusted to the needs of a specific patient group, specific application or medical situation. Another stated advantage of the composition is that "undigested starch is prevented from reaching the colon, where it would be digested by bacteria, resulting in the formation of gas, especially in the colon."

Preparation of starch compositions are described as "cornstarch and different excipients were dry mixed in a granulator and agglomerated with water or ethanol as granulation fluid, depending on the solubility of the granulations substance used. The dry granulate was pressed into tablets." In Example 1, native cornstarch is said to be mixed with 10% by weight potassium alginate in a high shear mixer and water is added as granulation fluid. Granules were then said to be wet sieved through a 1 mm sieve and dried. Dried granules were then said to be sieved through a 1 mm sieve and collected on a 0.5 mm sieve. A small amount of fat was said to be added (5-20%) to the granules. The composition is said to be used in the from of the granulate or pressed tablets of granulate.

U.S. Pat. No. 7,053,066 reports a food composition/food preparation method, which uses therapeutically effective amounts of additives such as hydrophilic substances (propylene glycol alginate as an example) and pharmaceutically acceptable salts in foods, to enhance the starch cell wall membrane that slows the enzymatic hydrolysis of starch resulting in controlled release of glucose. The invention relates to a method for treating overweight patients or patients with obesity.

U.S. published patent application 2006/0127453 reports a delivery vehicle suitable for carrying probiotic and bioactive compounds for aquatic animals. The vehicle is said to protect the active components from digestion and breakdown in the stomach. The delivery vehicle is described as microparticles or macroparticles comprising one or more non-digestible polymers and an emulsifier. The polymer is said to include among others starch, hemicellulose, cellulose, silicone, poly (vinyl alcohol), poly(ethylene oxide), poly(vinylpyrrolidone), and poly(hydroxyethylmethyacrylate). Descriptions of the use of starch to prepare the delivery vehicle as microparticles refer to the use of gelatinized starch. Microparticle formation by crosslinking a mixture of certain starches, emulsifier and alginate by dropping or spraying the mixture into a solution containing calcium ion is also described. The application also contains an example for the oral delivery of insulin to diabetics using a starch, emulsifier, alginate microparticle composition.

SUMMARY OF THE INVENTION

The present invention relates to entrapment of starch in a crosslinked polymer matrix in the form of microparticles, including microspheres. In specific embodiments, the polymer is a polysaccharide. The entrapped starch exhibits a significant decrease in the glycemic response and an extended release of glucose, and also serves as a source of starch-based dietary fiber for extended fermentation in the colon. Starch is the most desirable fermentation substrate for the colon due to its ability to generate high levels of butyrate, which has been shown to be beneficial for colonic health. The composition of this invention are distinct in structure from encapsulated starch in that the microparticles and microspheres containing starch do not have a shell-core structure in which the starch core is exposed to degradation only after the shell is broken down. The microparticles and microspheres of this invention are composed of a matrix formed from the crosslinked polysaccharide which contains starch entrapped in the matrix. This structure is believed to be responsible at least in part for the extended release of glucose in the small intestine, but also for the extended fermentation throughout the colon.

Microparticles and microspheres of this invention comprise a crosslinked polymer matrix entrapping starch or a mixture of starch and non-starch-based fiber. The non-starch-based fiber is preferably a fermentable fiber and can be a prebiotic material which provides benefit for promoting beneficial gut bacteria. The microparticles and microspheres can further comprise a copolymer which may be a water-soluble or non-water-soluble. The copolymer may be more soluble in acidic media than in neutral media. The crosslinked polymer matrix can be formed from crosslinking of one or more polymers. Preferably, the crosslinkable polymer(s) employed to form the matrix are ionically crosslinkable polymers, such as alginate, pectin, or chitosan. Microparticles and microspheres of this invention can also be coated after formation with a polymer coating (this may be a polymer that is the same or different from that of the polymer matrix or copolymer). Polymer coating can be formed from any edible polymer and is typically formed from a polymer that is non-digestible, slowly-digestible or that does not itself release glucose on digestion. Suitable coating polymers include among others chitosan. Microparticles and microspheres of this invention can also be coated with starch, particularly slowly-digestible starch or low-amylopectin starch (high amylose starch).

The invention provides a method for forming microparticles and microspheres comprising entrapped starch which are useful for food and medicinal applications as described herein. In this method, an ionically crosslinkable polymer, such as an anionic or cationic polysaccharide, is dissolved in water and starch alone or in combination with a non-starch based fiber is added to the solution typically forming a suspension. The mixed suspension is contacted with a suitable ionic crosslinking agent such as a solution of divalent cations (e.g., an aqueous Ca ion solution) to form microparticles which have a crosslinked polymer matrix with starch entrapped within the matrix. In one embodiment, droplets of the mixed suspension are introduced into a solution containing ionic crosslinking agent and microparticles or microspheres formed are collected. The microparticles and microspheres as formed are believed to be in the form of a hydrogels. The collected microparticles or microspheres are optionally dried by heating at temperature of 45 C or less for a sufficient time to remove a desired amount of water. The microparticles or microspheres can be dried to a form that contains less than 5% moisture which can be rehydrated if desired prior to application.

In specific embodiments, the microspheres and microparticles contain 50% or more by weight of starch. In other embodiments, the microspheres and microparticles contain 75% or more by weight of starch. In specific embodiments, the crosslinked polymer represents 40% or less or 25% or less by weight of the microspheres and microparticles. In additional embodiments, the crosslinked polymer represents 10% or less by weight of the microspheres or microparticles. In specific embodiments, the ratio of starch to ionically crosslinked polymer in the microparticles or microspheres ranges from 3:1 to 50:1. In more specific embodiments, the ratio of starch to ionically crosslinked polymer in the microparticles or microspheres ranges from 4:1 to 40:1. In currently preferred embodiments microparticles consist essentially of starch and crosslinked polymer matrix. Ionically crosslinkable polymers useful in this invention include among others one or more alginates (alginic acids and salts thereof), pectins, gellans, carageenans, and chitosan (which can be crosslinked with anionic crosslinking agents, such as phosphate or sulfate). Microparticles or microspheres can be dried after formation to facilitate storage. Microparticles or microspheres can be used in this dry form as a food ingredient which is rehydrated on cooking. Alternatively, the microparticles or microspheres can be rehydrated and ingested. Alternatively the dries materials can be presses into tablets or pellets for administration.

The invention also provides microparticles and microspheres which comprise a copolymer in addition to the ionically crosslinked polymer. The copolymer is typically not a polymer that is ionically crosslinked under the conditions in which the microparticles and microspheres are prepared. For example, a cationically crosslinkable polymer, such as an alginate can be combined with a copolymer which is anionically crosslinkable, such as chitosan. The amount of copolymer included can range generally from about 0.5% to 50% of the total amount of crosslinkable polymer and copolymer. Useful copolymers include among others: polysaccharide gums such as gum Acacia, gum Arabic, gum Tragacanth, and guar gum, cellulose, cellulose ethers (including among others hydroxypropylmethylcellulose), and agar. In specific embodiments, the ratio of starch to combined ionically crosslinked polymer and copolymer in the microparticles or microspheres ranges from 3:1 to 50:1. In more specific embodiments, the ratio of starch to combined ionically crosslinked polymer and copolymer in the microparticles or microspheres ranges from 4:1 to 40:1. In specific embodiments, microparticles and microspheres comprise crosslinked polymer and copolymer with 50% or more by weight of starch. In specific embodiments, microparticles and microspheres comprise crosslinked polymer and copolymer with 75% or more by weight of starch. In currently preferred embodiments, microparticles and microspheres of this invention consist essentially of crosslinked polymer, copolymer and starch.

In related embodiments, the invention provides microparticles and microspheres containing non-starch based fiber, particularly non-starch based fermentable fiber, in addition to starch or in place of starch. In specific embodiments, the ratio of starch combined with non-starch based fiber to ionically crosslinked polymer optionally combined with copolymer in the microparticles or microspheres ranges from 3:1 to 50:1. In more specific embodiments, the ratio of starch combined with non-starch based fiber to ionically crosslinked polymer optionally combined with copolymer in the microparticles or microspheres ranges from 4:1 to 40:1. In embodiments in which starch is combined with a non-starch based fiber, the combined amount of starch and non-starch based fiber in the microparticles or microspheres is 50% or more by weight. In other embodiments, the combined amount of starch and non-starch based fiber is 75% or more by weight. In specific embodiments, the ratio of starch to non-starched based fiber can range from 1:100 to 100:1. Non-starch based fiber useful in the compositions of this invention includes beta-glucan from various sources, dextrins, pectin, chitosan, gum Arabic, guar gum, cellulose, xanthan gum, fructans, and prebiotics such as various oligosaccharides, including fructo-oligosaccharides, inulins, corn fiber gum, lactilol, lactosucrose, lactulose, polydextrose, pyrodextrins.

The starch compositions of the present invention are useful for creation of food products with varying starch digestion properties and as a source of dietary fiber. These compositions are useful as food ingredients particular ingredients in food that will be cooked prior to ingestion. It has been found that the compositions of this invention retain the extended glucose release and extended fermentation properties after cooking. In specific embodiments, the starch in the slow glucose release compositions and fermentable fibers of this invention is uncooked starch.

The starch-based microparticles and microspheres of this invention are useful as foods, as food ingredients for food preparation, and as prophylactic or therapeutic compositions for prevention and/or treatment of diseases of the colon. The starch-based microspheres or microparticles of this invention are also useful in the preparation of foods with potential health benefits for diabetes, prediabetes, cardiovascular disease, and obesity. The starch-based microparticles and microspheres provide a prebiotic fiber material which provides benefit for colon health and which in particular is useful to prevent and treat gut inflammation The starch-containing compositions of this invention provide slowly-available glucose materials for diabetics are useful for prevention of hyperglycemia (an increase in blood glucose levels), hypoglycemia (reduced blood glucose concentrations) and patients with certain metabolic disorders such as glycogen storage disease type I (GSD1).

The starch-containing compositions of this invention provide slow and prolonged release of glucose which can be beneficial to mental performance.

The compositions of the microspheres and microparticles of this invention can be varied as described herein to selective vary the digestibility of the starch therein as measured by the amounts and relative amounts of RDS, SDS and RS exhibited by the compositions.

The invention further provides methods for maintenance of colonic health by oral administration (by ingestion) of compositions of this invention comprising starch. The invention also provides methods for the prevention and/or treatment of diseases of the colon by oral administration (by ingestion) of compositions of this invention containing starch or a mixture of starch and non-starch based fiber.

Other aspects and embodiments of the invention will be apparent on consideration of the specification as a whole including the drawings, detailed description and examples.

BRIEF DESCRIPTION OF THE DRAWINGS

FIGS. 6A-D are scanning electron microscopy (SEM) pictures illustrating surface and core of the polymer-entrapped starch and the mechanism of the starch digestion therein.

DETAILED DESCRIPTION OF THE INVENTION

The invention relates to slowly digestible and slowly fermentable starch compositions. The compositions of the invention are composed of a crosslinked polymer matrix with starch entrapped in the matrix. The polymer matrix is preferably formed by crosslinking of an ionically crosslinkable polymer. The composition is formed as microparticles which generally range in size (typically an average particle size) from tens of microns to thousands of microns in size. More specifically, the microparticles of the compositions range in size from 20 microns to 5000 microns (5 mm) and yet more specifically from 50 to 2000 microns. Microparticles may be formed as microspheres having a spherical shape. As formed in aqueous media, the microparticles comprise a hydrogel of the ionically crosslinked polymer with entrapped starch. The wet microparticles can be employed in the various applications described herein or the particles can be dried without loss of function and rehydrated prior to optional cooking and ingestion. Dried microparticles are also useful and may for example be pressed into tablets or formed into or combined in various dosage forms.

It will be appreciated in the art that particle size of starch compositions is dependent upon the size of starch granules that are used. Corn starch granules range in average size between 20 and 45 micron. In applications where smaller microparticles are desirable, starch granules which are smaller in size such as rice (10 micron) or amaranth starch (1-3 micron) can be used.

The starch-entrapped microparticles optionally comprise one or more copolymers, one or more non-starch based fibers which may be fermentable, and/or one or more prebiotic materials. Microparticles of the invention optionally comprise non-caloric sweeteners, and/or flavoring agents which do not affect the functional properties of the microparticles with respect to digestion and fermentation. In a preferred embodiment, starch compositions of this invention do not contain emulsifiers. Emulsifiers are not required for the functional properties of the microparticles with respect to digestion and fermentation.

The starch compositions of this invention are intended for oral administration, ingestion and for use as food products or as ingredients in food products. All components of the compositions herein must be suitable for food applications or recognized as safe for such applications.

Starch-containing microparticles are prepared by contacting drops or droplets of a suspension or solution containing a crosslinkable polymer and starch with a suitable crosslinking agent. Drops or droplets are formed for example by any means know to the art and in particular, drops or droplets formed by passing the suspension of solution through an orifice, such as that of a hypodermic needle or those formed by air atomization of the suspension of solution. The suspension or solution from which drops or droplets are formed is preferably a homogenous mixture of starch and the crosslinkable polymer or a mixture of the crosslinkable polymer with one or more copolymers. Drops or droplets are contacted by any known means with a suitable crosslinking solution. Drops or droplets can for example be dropped into or injected into the crosslinking solution. On contact with the crosslinking agent, a crosslinked polymer matrix is formed wherein the starch is entrapped in a continuous matrix of the crosslinked polymer.

The crosslinkable polymer may be a mixture of two or more of such polymers wherein crosslinking of both polymers in the mixture is chemically compatible. When mixtures of crosslinkable polymers are employed, mixtures of crosslinking agents (assuming chemical compatibility) may be employed if desired or needed.

The crosslinkable polymer is preferably an ionically crosslinkage polymer wherein crosslinks are formed on contact with a suitable ionic species. In specific embodiments, the ionically crosslinkable polymer is an anionic polymer, such as an alginate, pectin, gellan or carrageenan which can be crosslinked on contact with a cation. Preferred cationic crosslinking agents depend upon the polymer to be crosslinked. For example, alginates, pectins and gellans are preferably crosslinked with a divalent or trivalent cation, in particular $Ca^{2+}$ or $Ba^{2+}$. In contrast, carageenans are more preferably crosslinked using a monovalent cations, such as $K^+$. In specific embodiments, the ionically crosslinkable polymer is water soluble.

In other specific embodiments, the ionically crosslinkable polymer is a cationic polymer, such as a chitosan, which can be crosslinked by contact with an anionic crosslinking agent. Suitable crosslinking agents for chitosan include citrate, phosphate and sulfate, among others.

It will be appreciated by those of ordinary skill in the art that it may be necessary or beneficial to adjust the pH of the starch-polymer-containing solution to achieve crosslinking.

In specific embodiments, the crosslinked polymer of the matrix of the microparticle is non-digestible (digestion herein is defined with respect to human digestion). In specific embodiments, the crosslinked polymer is non-digestible and non-fermentable in the colon. In other embodiments, the crosslinked polymer of the matrix is non-digestible, but is fermentable. In this case, the polymer matrix of the microparticle provides function as a fermentable fiber.

In specific embodiments, the starch-containing microparticles of this invention further comprise a copolymer. In specific embodiments, the copolymer is not an ionically crosslinkable polymer. In specific embodiments, the copolymer is not water soluble. In specific embodiments, the copolymer is water soluble.

The starch-containing microparticles and microspheres of this invention exhibit health benefits due at least in part to their digestibility profile. The starch-containing microparticle and microspheres of this invention can also be used to deliver other therapeutic or medicinal compounds via oral administration. However, in specific embodiments, starch-containing microparticles and microspheres of this invention do not carry drugs or other medicinals, other than starch, fermentable or non-fermentable fiber, and polymers described above. The microparticles and microspheres of this invention may include non-caloric sweeteners, low caloric sweeteners or flavoring agents Starch includes all starches as they are extracted from any and all plant sources. Native starches include all starches as found in nature in any plant source. Starches can also be obtained from plants which are obtained by standard plant breeding methods as well as by mutagenesis and genetic engineering or by combination of mutagenesis and genetic engineering with standard plant breeding methods. Plant sources for starches include cereals, legumes, tubers, roots, leaves and fruits. Starch can be extracted from corn (maize), rice, barley, wheat, oat, sorghum, oat, pea, sago, tapioca (cassava), arrowroot, sweet potato, yams, and banana, for example. Starches can be extracted from various mutant plants which exhibit alterations in starch phenotype. Starch also includes commercial starches that may be washed, bleached or otherwise treated to remove undesired components.

Starch is composed of two broad classes of polymers, amylose and amylopectin which are assembled to form a starch granule. The lower molecular weight amylose is a mainly linear polymer of alpha 1-4 bonded anhydroglucose units while amylopectin is a branched polymer comprised of linear chains of alpha 1-4 linked anhydroglucose units with branches resulting from alpha 1-6 linkages on the linear chains. Amylose readily reassociates or retrogrades following gelatinization to form less digestible starch material. Commercial resistant starches include those which are highly retrograded amylose. Amylopectin, which is much larger than amylose, is highly branched structure that retrogrades and crystallized much slower and less completely than amylose. Amylopectin is generally highly digestible even after reassociation. Native starch from different types of plants generally may contain different percentages of amylose and amylopectin, different size starch granules and different polymeric weights for amylose and amylopectin. As a result, native starch from different plant sources may have significantly different properties. Typically, the amylose content of starches ranges from about 15% to about 35%. Waxy starches contain higher levels of amylopectin (90% by weight or more) and are extracted from plants such as waxy maize, waxy rice, waxy barley, waxy sorghum and waxy wheat. High amylose starches contain greater than about 50% by weight amylose. High amylose starch can be subdivided into starches containing between about 50 to 60%, 70 to 80% by weight amylose and very high amylose starches which have 95% or more by weight amylose. In general, all such native and non-native starches, and mixtures thereof, are useful as in the methods and compositions herein. A portion of the starch employed in this invention can be resistant starch, which a starch or starch derivative which is not digestible in the small intestine. Officially the term is reserved for the sum of starch and products of starch degradation not absorbed in the small intestine of healthy individuals. Resistant starches can be physically inaccessible starch (RS1, e.g. trapped in seeds), granular starch (R2), highly retrograded starch (R3) and chemically modified starch (R4).

Starches include high-amylose starch and amylose starch and mixtures of such starches with native starches, particularly native corn starch. In specific embodiments, the starch can be or contain a waxy starch, particularly a waxy corn starch. In another specific embodiments, the starch can be a starch exhibiting an altered amylopectin structure obtained from a plant mutant or variant, such as wx, aewx, duwx, suwx, aedux corn mutants or analogous mutants having altered amylopectin of other plants. Of particular interest are starches in which the amylopectin is characterized by having a higher proportion of longer chain branches than are typically found in the amylopectin of native starches. See: Obanni, M. and BeMiller, J. N.(1995) Identification of starch from various maize endosperm mutants via ghost structures. Cereal Chemistry 72:436-442 and references therein for description of maize mutants. Starches also include mixtures of different starches, for example, to obtain a starch having a desired amylose level.

Polymer, as used herein, includes various edible natural and synthetic biopolymers and their derivatives including cationic biopolymers, anionic biopolymers, and amphoteric molecules. Crosslinker for the purpose of the present invention includes any chemical agent permitted for food use and used within the legal limit. Preferably the polymer is ionically crosslinkable and is a polysaccharide. Preferably, the crosslinking agent is a cation (mono-, di- or trivalent) or an anion.

Alginate refers generally to alginic acid, and the salts of alginic acid. Alginate is obtained from brown algae typically as sodium alginate which is water soluble. Alginate is crosslinked by contact with di- or trivalent cations such as $Ca^{2+}$ or $Ba^{2+}$. The alginate derivative propylene glycol alginate may be employed as a copolymer in the compositions of this invention but is not preferred for use to form the crosslinked polymer matrix of the microparticles. Alginate is not digestible and is not extensively fermented in the human colon.

Gellan or gellan gum is a water-soluble bacteria polysaccharide. In its gelled or crosslinked form it is heat resistance which may provide additional benefit for its use in applications which require cooking. Gellan is crosslinked with divalent cations. Gellan is highly terminable.

Pectins are complex heteropolysaccharides which can be crosslinked with divalent cations, such as $Ca^{2+}$. Pectins are available from a variety of plant sources and can contain different degrees of esterication. Pectins with a low level of esterification (low-methoxy pectins) are preferred for crosslinking with cautions, such as $Ca^{2+}$. Pectin is water soluble but is not digestible. In contrast, pectin is highly fermentable.

Carrageenan is a highly anionic water-soluble gum obtained from red seaweed. Certain carageenans (kappa- and iota-carageenans) form gels on contact with cations, such as $K^+$ and $Ca^{2+}$. Sodium salts of carageenans are watersoluble Carrageenan are non-digestible but are fermentable.

Chitosan is a linear cationic polysaccharide which is gelled or crosslinked in the presence of anions, such as citrate, phosphate or sulfate Chitosan is soluble in acidic medium. Chitosan is not digestible, but is fermentable.

Dietary fiber is indigestible by definition and can classified as soluble or insoluble as is known in the area and can further be characterized as fermentable by the bacteria flora of the colon or non-fermentable. Non-fermentable fiber includes among others methyl cellulose. Compositions of this invention provide a source starched based fermentable fiber. The starch in the compositions of this invention is only partially digested in the stomach and small intestine and is available for fermentation in the colon. Compositions of this invention provide a starch-based source of slowly fermentable fiber. Starch in the compositions of this invention which is not digested is available for fermentation in the colon, but has been found to be only slowed fermented and will not as a consequence result in bloating and significant rapid gas formation on passage into the colon. Compositions of this invention may include in addition to starch non starch based fermentable fiber in addition to any fermentable fiber that is provided In the polymer matrix and copolymers of the composition. A variety of fermentable fibers are known in the art. A preferred form of fermentable fiber is prebiotic materials which promote the growth of such beneficial bacteria in the gut.

U.S. Pat. 6,248,375, provides examples of dietary fiber, including soluble and insoluble fiber, as well as fermentable and non-fermentable fiber.

Microparticles formed on crosslinking are incubated in the crosslinker solution over a period of 1-24 hr to permit maximum crosslinking of the polymer, thereby improving the product recovery and functionality. The microparticles are then washed to remove the crosslinker, free starch and free polymer. The washed microparticles are optionally dried, preferably, but not restricted to, in a hot-air oven at 45° C. The washed microparticles may be kept hydrated and stored for later use. Dried microparticles can be stored for later use and rehydrated as desired.

Total starch (TS) content of the starch-entrapped microparticles is estimated using the Megazyme Total Starch Kit (Megazyme International Ireland Ltd., Wicklow, Ireland). All samples were powdered to a homogeneity using a ball mill prior to TS analysis. Starch entrapment efficiency was calculated from the actual amount of starch in the dry microparticles and the total amount of starch used for encapsulation process.

Starch-entrapped microparticles, for the purpose of determining the extent of RDS, SDS and RS in the Englyst assay, are cooked by adding a certain amount of water and placing the sample in a boiling water bath for 20 min. Starch digestibility is expressed as % RDS (rapidly digestible starch, 20 min), % SDS (slowly digestible starch, 120 min-20 min) and % RS (resistant starch, >120 min) obtained in the Englyst assay (Englyst et al., 1992).

For the purpose of inclusion of the starch-biopolymer microparticles in foods, cooking processes could include standard cooking procedures, such as boiling water, pressure cooking, and dry and moist heat processing including baking and roasting.

Starch-containing microparticles and microspheres of this invention can be used as a starch-based ingredient for various food and pharmaceutical preparations and any applications wherein uncooked or cooked starch is traditionally used.

The invention provides a method for obtaining a starch composition having a desired starch digestion profile. The method involves preparation of ionically crosslinked microparticles in which starch is entrapped within the crosslinked polymer matrix wherein one or more of the type and concentration of starch employed, the type and concentration of ionically crosslinkable polymer employed, the type and concentration of optional copolymer employed, the type and concentration of optional non-starch based fiber added, and the type and concentration of crosslinking agent are selected to achieve the desired starch digestion profile. The method may, in alternative to, or more typically, in addition to selection of types and relative concentration of components, also involve selection of the size of the microparticles or microspheres, variation of the incubation time of the microparticles and microspheres in crosslinking solution, and/or the concentration of crosslinking agent employed. The method also optionally include providing the microparticles or microspheres with a coating which can affect digestion profile. Particle size can be adjusted, for example, by adjusting the size of drops or droplets which contact the crosslinking solution. This may be achieved by adjusting the orifice size which delivers the droplets. Alternatively, the process may provide a range of droplet sizes by atomizing the starch/polymer solution prior to contact with the crosslinking solution. To obtain a desired range of particle sizes or a desired average particle size, sieving or filtration methods may be used.

For purposes herein the term starch digestion profile of a starch-containing composition is defined as the relative amounts of RDS, SDS and RS measured employing the Englyst method (Englyst et al., 1992, 1996). These measurements have been found to correlate with in vivo starch digestion in humans. The desired profile of starch digestion depends in general upon goal of a given application. In general, the methods herein can be used to adjust the digestive profile of the starch-compositions so that it differs from that of the starch or starch mixture entrapped in the composition.

Figure 10:
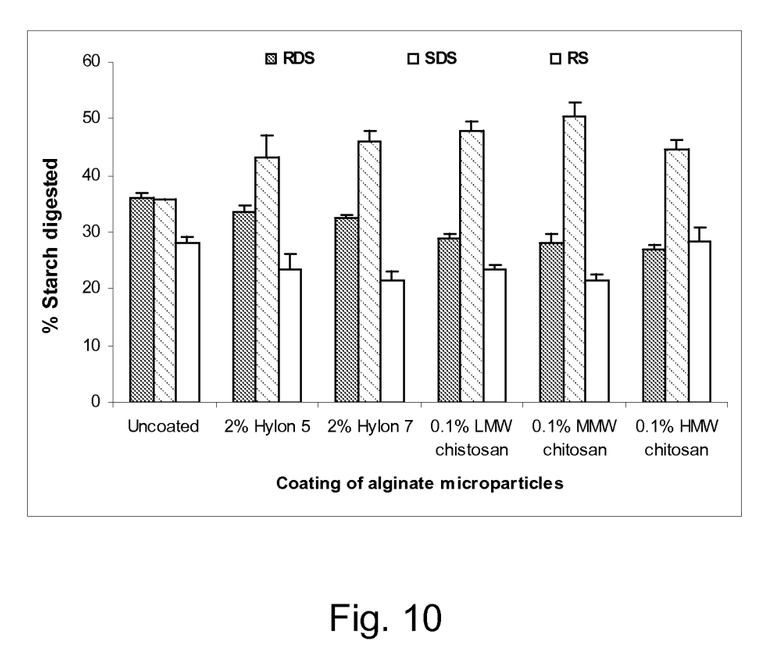
FIG. 10 is a graph illustrating how different polymer coating(s) of the microparticles can modify starch digestibility

If controlled-release of glucose on starch digestion is the main goal and provision of fermentable fiber in not desired, then it is desired to minimize both RDS and RS so that SDS predominates in the profile. Such a profile may be desired for applications to food products for diabetics and pre-diabetics. For example, one or more of the following can be selected: the particle size can be adjusted to the sub-millimeter range (e.g. 0.05 to 0.5 mm), alginate or combinations of alginate with cellulose ether can be employed and the amylopectin content of the starch can be increased somewhat compared to normal corn starch. Additionally, the relative amount of SDS can be enhanced by providing the microparticles with a coating as illustrated in FIG. 10.

If it is desired to provide a balance of controlled-release as well as providing slowly fermentable fiber that compositions in which, then it is desired to minimize RDS and provide a balance of both SDS and RS. For example, one or more of the following can be selected: particle size can be adjusted to the sub-millimeter range (e.g., 0.05 to 0.5 mm), alginate alone or in combination with a cellulose ether (e.g., hydroxypropylmethylcellulose) can be employed and/or the amylose content of the starch can be increased somewhat compared to normal corn starch to reduce RDS.

If it is desired to provide fermentable fiber as the main goal of a composition, then it is desired to maximize RS. For example, if it is desired to maximize RS in a composition, one or more of the following can be selected: particle size can be selected to be in the millimeter range (e.g., greater than 0.5 mm), the amylose content of the starch used can be increased (e.g., high-amylose starch or a mixture of native corn starch and high-amylose starch can be used), chitosan may be employed in the composition as a copolymer in combination with a anionic crosslinkable polymer such as alginate.

The various parameters listed above can be readily varied in the methods of this invention by one of ordinary skill in the art as described herein to provide various starch-containing compositions in which starch is entrapped within a crosslinked polymer matrix. Starch digestion profiles measuring RDS, SDS and RS of such compositions can be assessed as described herein and as illustrated in the examples herein to produce starch compositions having desired starch digestion profiles.

Figure 9:
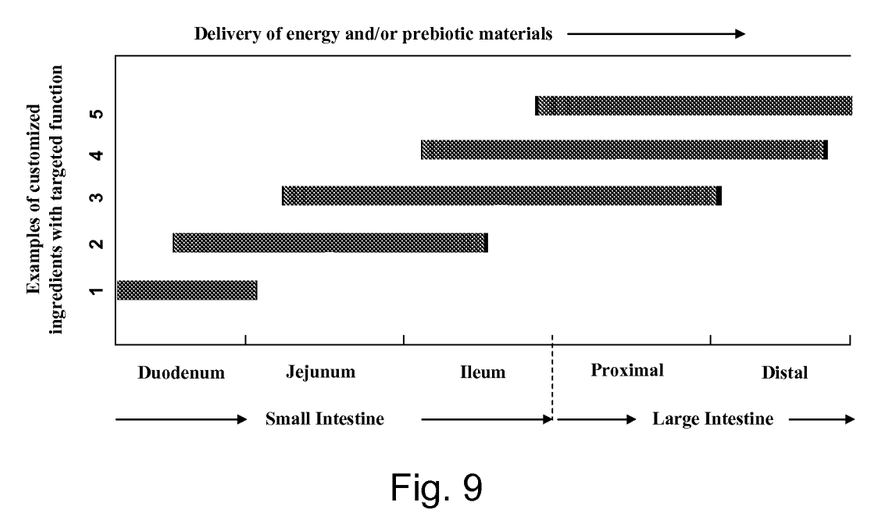
FIG. 9 is an illustration of targeting of starch compositions of this invention to different regions of the small intestine and colon.

The invention also provides a related method for targeting glucose and/or fermentable fiber to regions of the small intestine or colon. FIG. 9, illustrates the regions in the intestinal tract to which glucose and/or fermentable fiber can be targeted. In a specific embodiment, the method targets a prebiotic material to the proximal or distal region of the colon. Fermentable fiber and prebiotic materials are often very rapidly fermented on entering the colon in the proximal region. In a specific embodiment, starch-containing compositions of this invention can be employed to target fermentable fiber and/or prebiotic materials to the distal portion of the colon. The term "targeting" refers to the ability to increase the level of digestion of starch (in the small intestine) or the level of fermentation of starch in a selected region of the intestinal tract compared to the level of digestion or fermentation that would be observed of the starch component itself at that selected region. Thus, targeting of fermentable fiber to the distal region of the colon means that there will be increased fermentation of the fiber in the distal region of the colon with an increase in potentially beneficial fermentation products in the distal region of the colon. As described above, the method involves preparation of ionically crosslinked microparticles or microspheres in which starch is entrapped within the crosslinked polymer matrix wherein the types and relative concentration of one or more components, the size of the microparticles or microspheres, the incubation time of the microparticles and microspheres in crosslinking solution, and/or the concentration of crosslinking agent employed are selected to provide a starch-composition which exhibits desired targeting of glucose, fermentable fiber and/or prebiotics. The compositions can, for example, be prepared to maximize the amount of RS which functions as a fermentable starch and a prebiotic in the colon. Additionally, compositions can be prepared to provide for slow fermentation of the fermentable starch in the colon. The rate of fermentation of such compositions can be readily assessed as described herein in Example 9 by in vitro fermentation employing human fecal flora. Example 10 provides example compositions for targeting to selected locations in the intestinal tract. In general, targeting to the distal colon can be accomplished by increasing the size of the microparticles and microspheres, decreasing the ratio of starch to crosslinked polymer, adding copolymers such as chitosan to the composition and employing starch with higher amylose levels.

The solubility properties of the copolymer may also be selected to affect targeting and digestion. For example, copolymers with limited water-solubility may be employed. Copolymers which exhibit differences in solubility dependent on pH can also be employed. For example, chitosan does not dissolve in water at neutral pH. Chitosan dissolves at pH <6.5 (typically in acidic environments). Chitosan employed in microparticles of this invention can dissolve in the acid environments of the stomach leading to localized increase in the viscosity inside the microparticles, which in turn leads to slow enzyme movement inside the beads and hence slow digestion/fermentation.

Therefore, the present invention offers several distinct benefits over previously available foods by permitting the design of starch-entrapped microspheres with a tailored range of glucose release profiles for a variety of applications including diabetic and pre-diabetic foods, satiety-inducing foods, athletic performance-inducing foods, cholesterol- and serum triglyceride-lowering foods, foods specific to cardiovascular health, foods designed for improved mental performance. Moreover, it also permits the creation of suitable starch-based dietary fiber material for colonic health. Additionally, the present invention facilitates delivery of fermentable fiber including prebiotics to the distal colon.

Certain compositions of this invention which contain higher levels of RS function as fermentable fiber for use alone or as ingredients in food products to provide the benefits of fermentable fiber. The starch-containing compositions of this invention which exhibit higher levels of RS also function as prebiotics, at least in part, because they are fermented in the colon to produce generally higher levels of butyrate than non-starch based fibers. In specific embodiments, compositions of this invention which are particularly useful as fermentable fibers and prebiotics are those that exhibit RS levels of 25% or more and 50% or more Compositions of this invention are useful as prophylactic and therapeutic agents for treatment of various diseases or conditions of the colon. For example, the compositions of this invention can be used for the prevention and treatment of diverticulosis, irritable bowel syndrome, inflammatory bowel disease, pouchitis, colitis including ulcerative colitis and chronic or recurrent colitis associated with *Clostridium difficile*, constipation, functional diarrhea, post traveler diarrhea syndrome (post-infectious irritable bowel syndrome), antibiotic associated diarrhea, and bloating. Compositions of this invention can be used in prophylactic compositions for prevention of colon polyps, colon cancer, and for maintaining remission in Crohn's disease. The compositions herein also have potential for treatment of atopic diseases (e.g. allergic dermatitis). Compositions herein including those containing one or more prebiotic material are useful in the prevention of bacterial overgrowth and fungal overgrowth, such as Candidiasis. Compositions herein may also be useful in the treatment of leaky gut (i.e., increased intestinal permeability associated, for example, with alcoholic liver disease) and/or NASH (non-alcoholic steatohepatitis associated, for example, with obesity). The compositions of this invention which exhibit slow digestion and/or slow fermentation are particularly useful for the treatment of colon inflammation and for the prevention of dysbiosis.

The present invention provides methods of treating disorders, diseases conditions, particularly diseases of the colon, in a mammal and particularly in a human, by oral administration of a therapeutically-effective amount of a starch-containing composition of this invention to an individual in need of treatment or prophylaxis. The result of treatment can be partially or completely alleviating, inhibiting, preventing, ameliorating and/or relieving the disorder, condition or one or more symptoms thereof. Administration is by oral ingestion. An individual in need of treatment or prophylaxis includes those who have been diagnosed to have a given disorder or condition and to those who are suspected, for example, as a consequence of the display of certain symptoms, of having such disorders or conditions.

Diabetes mellitus is a group of metabolic diseases where, due to insulin defects (either due to lack of insulin secretion or insulin action or both), the blood glucose levels remains elevated (hyperglycemia) for longer periods of time as compared to an healthy individual. Chronic hyperglycemia can result in damage to various cells, tissues and organs. The present invention provides starch-containing materials (microparticles and microspheres with entrapped starch) which provide for slow release of glucose on ingestion. Use of slowly available glucose materials can result in a more controlled glucose uptake thereby decreasing the glycemic fluctuations thereby help maintaining glucose homeostasis in the body. Thus, the starch-containing materials of this invention are useful as food products and food ingredients useful for diabetics and for use as medicaments or therapeutics for diabetics.

Recent studies have shown that rapidly and slowly available glucose from foods can affect secretion and action of gastrointestinal hormones. For example, Wachters-Hagedoorn et al. (2006) showed that luminal glucose provided through foods may be an important factor triggering a cascade of postprandial metabolic events including the stimulation of the incretin hormones [glucagon-like peptide-1(GLP1) and glucose-dependent insulinotropic polypeptide (GLP)]. Gastrointestinal hormones are secreted by the endocrine cells throughout the mucosa of the gastrointestinal tract, and affect various processes including gastrointestinal motility, digestion, and absorption to name a few. Hormones such as cholecystokinin (CCK) affect pancreatic function, while GIP and GLP1 affect insulin secretion and gastric emptying effects. Further, other hormones such as peptide tyrosine-tyrosine (PYY) has also been suggested to affect pancreatic function and regulation of food intake. The ability of the slowly digesting starch microparticles and microspheres of this invention to target and release glucose in different areas of the small intestine could significantly influence stimulation and action of gastrointestinal hormones providing beneficial health effects such as satiety and thereby weight management, energy balance, and performance.

The term "therapeutically effective amount," as used herein, refers to the amount of a starch-composition, when administered to an individual typically over a selected time period is effective to at least partially treat a disorder, disease or condition from which the individual is suffering, or to at least partially ameliorate a symptom of such disorder, disease or condition. The compositions herein may useful for administered to those who have been diagnosed as having a disorder and to those who exhibit symptoms consistent with a disorder. The term also applies to amounts of the composition which are useful for achieving a protective or prophylactic effect. As is understood in the art, the therapeutically effective amount of employed, will depend upon the specific disorder or condition, and the specific individual to whom the compound is to be administered (age, weight, condition, sex, etc.).

The oral dosage requirements needed to achieve the "therapeutically effective amount" vary with the particular compositions employed, the severity of the symptoms presented and the particular subject being treated. Because the starch-composition is intended for oral administration, at least in part expresses its benefit by its digestion, and at least in part functions as a food, the daily dosage will depend upon the nutritional requirements of the individual being treated. Administration may in the form of a food product or food additive which is ingested at regular intervals (e.g., meal times) in an amount consistent with the nutritional needs of the individual. Generally, compositions of this invention are intended for at least daily administration over an extended period of time to provide prophylactic benefit, therapeutic benefit or both.

When a Markush group or other grouping is used herein, all individual members of the group and all combinations and subcombinations possible of the group are intended to be individually included in the disclosure. When a group of chemical compounds, species or compositions is disclosed herein, it is understood that all individual members of that group and all subgroups, including any isomers, enantiomers, and diastereomers of the group members, are disclosed separately. It is intended that all combinations and subcombinations of the specific groups disclosed herein are individually included in this disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in diagnostic assays and in therapeutics. Methods for making such isotopic variants are known in the art. Specific names of compounds are intended to be exemplary, as it is known that one of ordinary skill in the art can name the same compounds differently.

Molecules disclosed herein may contain one or more ionizable groups from which a proton can be removed (e.g.,-COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference to the extent that there is no inconsistency with the disclosure of this specification. Some references provided herein are incorporated by reference to provide details concerning sources of starting materials (e.g., crosslinkable polymers, copolymers, fermentable fiber, crosslinking agents), sources and types of starches, sources and types of fiber, additional starting materials, additional reagents, additional methods of synthesis, additional methods of analysis, additional biological materials, additional crosslinkable polymers, additional copolymers and additional uses of the invention.

THE EXAMPLES

Example 1

Entrapment of Starch in Alginate Microparticles/Microspheres

Effect of alginate concentration on efficiency of starch entrapment and digestion properties.

Sodium alginate (low viscosity, Sigma) was used to form microparticles. To 50 g water, a weighed amount of sodium alginate to obtain a 0-3% w/w solution was added, and then the mixture was stirred continuously to obtain a clear solution. Five grams of normal cornstarch (NCS) was added and mixed to form a homogenous suspension. Under continuous stirring, this mixture was dropped into a beaker containing 2% w/v calcium chloride solution ($CaCl_2$) at room temperature (25° C.) through a hypodermic needle using a peristaltic pump. The alginate spheres prepared were allowed to incubate for 2-3 hr in the 2% w/v $CaCl_2$ solution and then harvested by filtration. The collected beads were washed 3 times with distilled water and then dried for 12 hr in a hot air oven at 45° C.

A known weight of entrapped starch (~-200 mg equivalent starch) was cooked in water (Starch: water =1:10 w/v) by placing the tubes containing samples in a boiling water bath for 20 min. NCS was used as control. Samples were drawn at the desired time intervals and glucose release analyzed using a GOPOD assay kit (Megazyme International).

The efficiency of NCS entrapment was 91-99% indicating negligible loss of starch in the encapsulation process (Table 1). The microspheres retained structural integrity on both normal and pressure-cooking.

As the alginate concentration increased, RDS values dropped proportionally (r=−0.97) from 75% to 15% respectively (Table 1). Since RDS values obtained from the Englyst assay correlate to glycemic index (GI) of food consumed in humans (Englyst et al., 1996), this study indicated that such a preparation results in lowering the glycemic index (GI) or glycemic response. Further, RS values increased from 1 to 70% with increasing alginate concentration (Table 1), indicating that the preparation also serves as a good source of fermentable fiber.

TABLE 1

| Starch:alginate | Efficiency (%) | Englyst Assay (%) | | |
|---|---|---|---|---|
| | | RDS | SDS | RS |
| 100:0 | 100 | 75.27 ± 1.76 | 23.53 ± 2.38 | 1.20 ± 0.61 |
| 40:1 | 96.95 ± 0.56 | 67.72 ± 1.35 | 25.13 ± 0.45 | 7.15 ± 1.79 |
| 20:1 | 97.78 ± 0.31 | 62.57 ± 2.64 | 33.26 ± 0.46 | 4.18 ± 2.18 |
| 10:1 | 99.31 ± 0.22 | 40.16 ± 0.96 | 43.51 ± 1.15 | 16.33 ± 0.19 |
| 5:1 | 94.07 ± 0.42 | 21.94 ± 0.01 | 37.95 ± 0.54 | 40.10 ± 0.54 |
| 10:3 | 91.50 ± 2.50 | 14.39 ± 0.53 | 15.04 ± 0.01 | 70.57 ± 0.54 |

All data expressed as mean ± standard deviation

Example 2

Effect of Sphere Size on Starch Digestibility.

Figure 1:
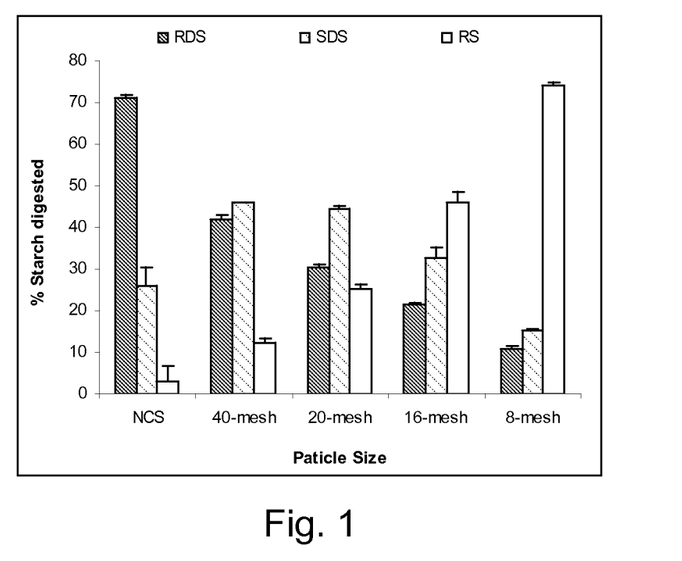
FIG. 1 is a graph of the effect of starch-biopolymer microparticle size on starch digestibility.

Samples were prepared as in Example 1 using 2% alginate solution and NCS. Starch microspheres of different sizes were prepared by atomizing the alginate-starch homogenous suspension into the 2% w/v calcium chloride solution. The size of the cooked starch spheres influenced starch digestion rate (FIG. 1). A decrease in sphere size (8- to 40-mesh) resulted in an increase in both RDS (15% to 59%) and SDS (15% to 46%).

Example 3

Effect of Calcium Chloride Solution on Starch Digestibility

Figure 2:
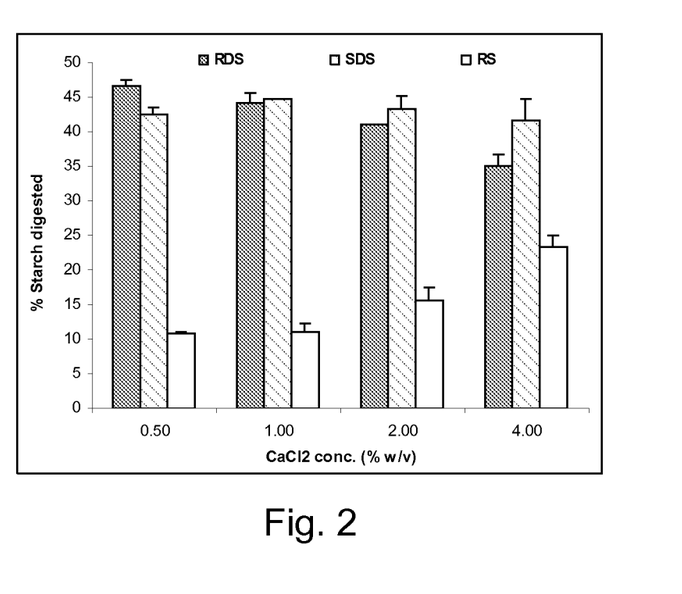
FIG. 2 is a graph of the effect of crosslinker ($CaCl_2$) concentration used on starch digestibility.

Samples were prepared as in Example 1 using 1% alginate solution and NCS and dropping the alginate-starch homogenous suspension into a calcium chloride solution at various concentrations (0.5-4.0% w/v). As illustrated in FIG. 2, increasing $CaCl_2$ concentration (0.5% to 4%) resulted in a small decrease in RDS with a corresponding increase in RS. SDS values, however, did not change significantly.

Example 4

Figure 3:
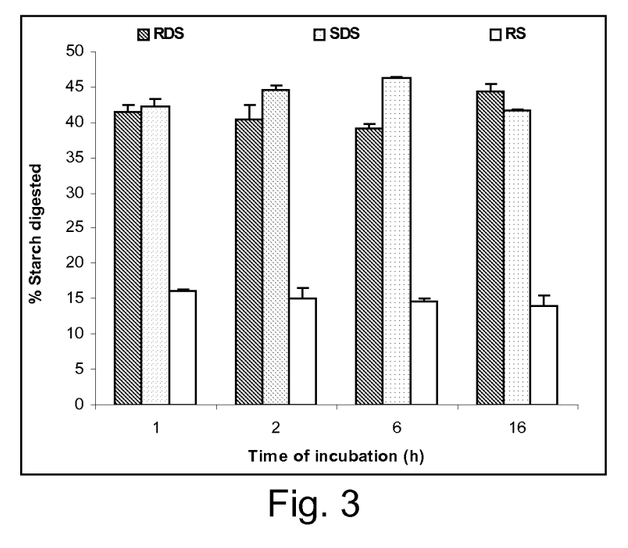
FIG. 3 is a graph of the effect of incubation time of the prepared spheres in the crosslinker ($CaCl_2$) solution on starch digestibility.

Effect of Incubation Time of the Prepared Spheres in the $CaCl_2$ Solution on Starch Digestibility Samples were prepared as in Example 1 using 1% alginate solution and normal corn starch and dropping the alginate-starch homogenous suspension into a 2.0% w/v calcium chloride solution bath. The spheres thus prepared were incubated in the calcium solution for varying time intervals (1-16 h) prior to washing and drying. As illustrated in FIG. 3, incubation time did not significantly affect starch digestibility.

Example 5

Figure 4:
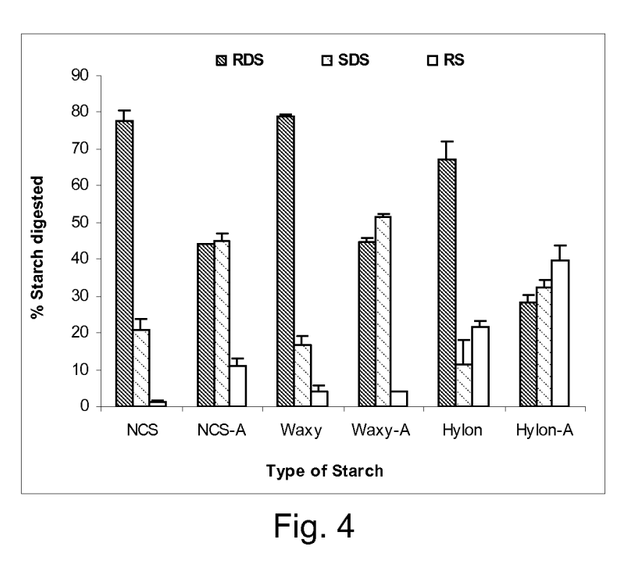
FIG. 4 is a graph illustrating how the digestion profile can be manipulated depending on type of starch used for entrapment.

How Different Types of Starch used in the Invention Resulted in Preparations with Desired Digestion and Fermentation Properties Samples were prepared as in Example 1 using 1% alginate solution and various starches by dropping the alginate-starch homogenous suspension into a 2.0% w/v calcium chloride solution bath. Results of these experiments are provided in FIG. 4. Increasing the amylose content of the entrapped starch decreased digestion.

Example 6

Use of a Different Polymers or a Combination of Polymers to Create Slowly Digestible Starches and Fibers.

Figure 5:
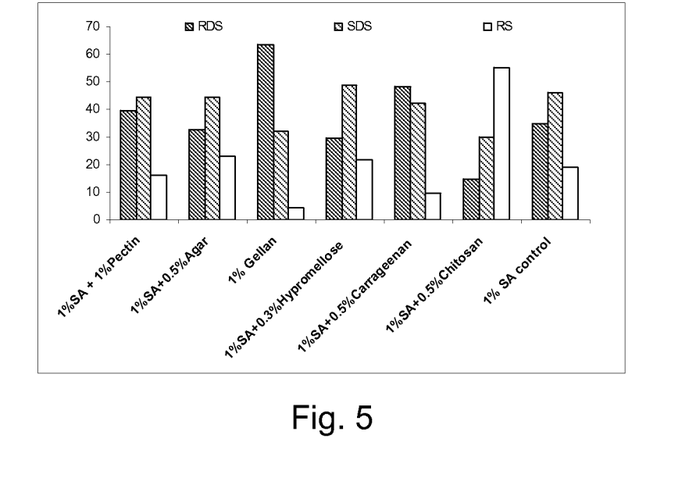
FIG. 5 is a graph of the use of a combination of polymers to create slowly digestible starches and fibers.

Samples were prepared as in Example 1 using 1% alginate solution and other polymers shown in FIG. 5 and normal corn starch and dropping the alginate-starch homogenous suspension into a 2.0% w/v calcium chloride solution bath. Varying RDS, SDS and RS values could be obtained by using other polymers or co-polymers for matrix preparation, blending or stabilization.

Example 7

Scanning Electron Microscopy (SEM) Picture Illustrating Surface and Core of the Polymer Entrapped Starch and the Mechanism of the Starch Digestion therein.

Surface and interior structure images of the fully hydrated spheres were determined using scanning electron microscopy (SEM). Control and digested spheres from Englyst assay were placed in a slit holder using cryo-adhesive and plunged into liquid nitrogen slush to freeze. Samples were then transferred to the preparation stage of the Gatan Alto 2500 cryo-system. The beads were fractured to reveal some internal surfaces and sublimed for 30-60 min. prior to coating with Pt (120 sec). Samples were imaged with an FEI NOVA nanoSEM FESEM operating primarily at 3 kV, aperture 6, spot size 3 and ~4.5-5.0 mm working distance. Magnifications were varied between 100 and 40,000x.

Figure 6A:
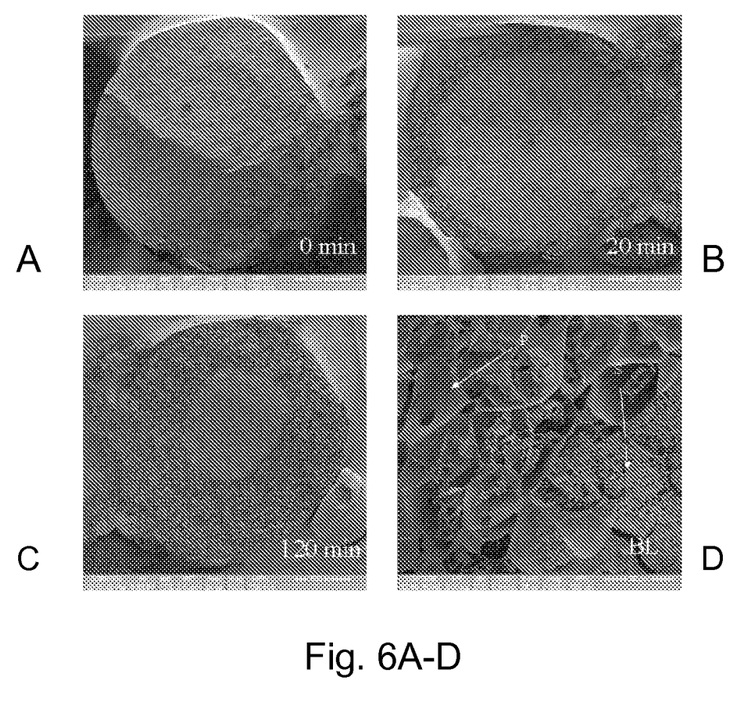

Scanning electron microscopy (SEM) figures at 0, 20 and 120 min FIG. 6A-C, respectively, show the crosssection of cryo-frozen digested microspheres. SEM micrograph (FIG. 6D) show the boundary layer (BL) between digested and undigested starch (S) moving towards the center of the microsphere over time (0, 20 and 120 min). Inner area for 20 and 120 min is the undigested starch. The outer porous layer is the polymer network (P).

These micrographs show that entrapment of starch in an alginate-calcium ion polymer matrix effectively creates a barrier to starch digestion (cooked in the entrapped form) by amylases and provides a slow glucose release matrix. Scanning electron microscope images show that the gelatinized starch trapped in the polymer matrix represents a highly dense food form which is gradually digested by the amylases from the periphery towards the center (outside to inside of the sphere). These micrographs illustrate that the microparticles and microspheres of this invention do not have a shell-core structure.

Example 8

Glycemic Response Curve of the Starch-biopolymer Microspheres in Healthy Human Subjects.

Sodium alginate (low viscosity) was used to prepare microparticles containing starch. To 990 g water, 10 g of sodium alginate (1% w/w solution) was added, and then stirred continuously to obtain a clear solution. To the biopolymer solution, 130 g of waxy corn starch (Tate & Lyle, Decatur, Ill.) was added and mixed to create a homogenous suspension. This mixture, while continuously stirred, was atomized into a 2% w/v calcium chloride solution ($CaCl_2$) at room temperature (25° C.) using an air atomizer (Spray Systems Co., Wheaton, Ill.). The starch-biopolymer spheres thus prepared were allowed to incubate for 12-16 h in the 2% w/v $CaCl_2$ solution and then harvested by filtration through sieve no. 80 (U.S.A. Standard Sieve Series). The collected spheres were washed several times with distilled water and then dried for 12 h in a hot air oven maintained at 45° C. Dried microspheres were sieved through the U.S.A. Standard Sieve Series (sieve nos. 8, 16, 20, 35, 40, 50 and 80 placed in that order from top to bottom) to collect different size fractions. Microspheres collected on the sieve no. 20 (1 part) and sieve no. 35 (2 parts) were mixed and used as a food ingredient for the human trial.

Total starch content of the microspheres was 80.94%. To 61.8 g (50 g starch equivalent) of microspheres placed in a mason jar, 400 ml water was added. The jar was then sealed and cooked (Presto® 18-Quart Pressure Canner (01751), National Presto Industries, Inc.) for 10 min at 10 pounds pressure. After cooking, the jars were allowed to cool to room temperature and stored at room temperature (~10-12 h) prior to use in the trial.

Glycemic response trials were conducted as per the procedure given in Wolever et al. (2005). Glucose was used as reference standard used for the calculation of glycemic index.

Nine active college-aged men and women (aged 20-23) in the normal-glycemic health were selected. Each subject was screened on two mornings on an overnight fast (>9hrs) within seven days of initiation of the trials. All data was collected between 6:30 and 11:30 am under random order on an overnight fast (9.5-14hrs). The average time to eat each meal was 2min 9sec and 15min 33sec for the glucose reference and the cooked microspheres respectively. Finger capillarized blood was collected in heparinized tubes in warmed fingers within ±3 min of the collection times (0,15, 20,45, 60, 90,120,150, and 180 min). Capillary blood glucose data was collected on a YSI Stat 2300 Plus analyzer. Capillary blood draws were performed in singlet, while glucose testing on each blood sample was performed in duplicate. Standards were captured each day with a coefficient of variation (CV) of <1%. The controls were captured each day within the manufacturer's recommendation with a CV of 1.5%.

Figure 7:
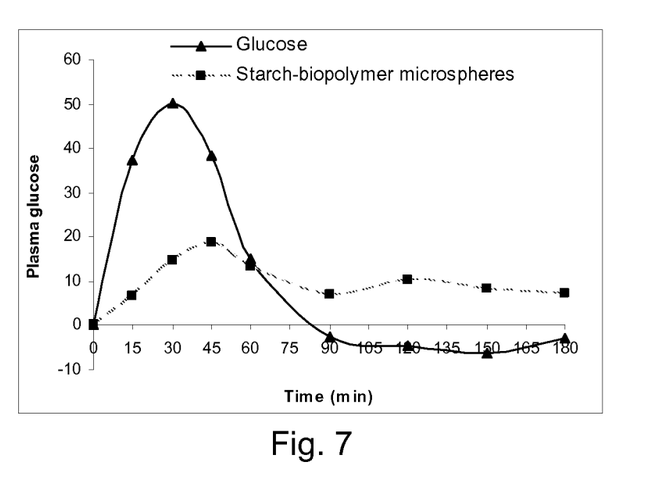
FIG. 7 is a glycemic response curve of the starch-biopolymer microspheres in healthy human subjects.

The AUC glycemic response curve was calculated according to the optimized method reported by Wolever et al. (2005). Glycemic response of the microspheres was much lower than the glucose reference and was also extended over a period of three hours of testing (FIG. 7). The glycemic index (GI) of the microspheres was calculated to be 57.4%. Moreover, there was extended glucose release.

Example 9

In vitro Fermentation Quality of the Pre-digested Starch-containing Microspheres Using Human Fecal Flora.

As indicated in FIG. 1, a large amount of starch remains entrapped in the microspheres after digestion. Therefore, to test the performance of the starch-containing microspheres under simulated large intestine conditions, samples were prepared as in Example 1 using 1, 2, and 3% alginate solution and NCS. A blank was also prepared using only 2% alginate. Samples of each type of microsphere (0.5 g) was cooked for 20 min in a boiling water bath, and then subjected, in triplicate, to in vitro digestion according to Lebet et al. (1998), with minor modifications: the simulated stomach acid was neutralized with 150 mM sodium bicarbonate, and the small intestine digestion time was increased to 3 h. Following digestion, the beads were washed several times with cold, distilled, deionized water, and transferred to 100 ml serum vials.

For in vitro fermentation, freshly voided feces were pooled from 3 healthy volunteers, and homogenized with anaerobic media (1:15 w/v) (Eller et al., 1971) under continuous carbon dioxide flushing. Following filtration through 4 layers of cheesecloth, 40 ml of homogenate were added to the serum vials containing the digested beads and anaerobically sealed. A sample of cooked NCS (300 mg) was also included as a control. The vials were incubated with gentle shaking at 37° C. After 0, 4, 8, 12, and 24 hr of fermentation, total gas volume was measured using a graduated syringe, and an aliquot of liquid was removed for short chain fatty acid quantification (Playne et al., 1985).

Figure 8:
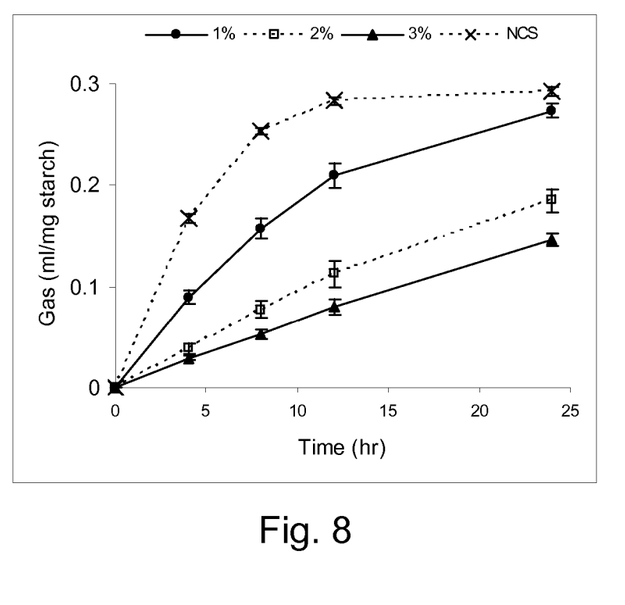
FIG. 8 is a plot of gas production versus time during in vitro fermentation of pre-digested starch-containing microspheres using human fecal flora.

Total gas volume and short chain fatty acids were reported as ml or μmol/mg starch remaining after digestion, respectively, and the blank containing only 2% alginate was subtracted from each value. Increasing the concentration of alginate used to create the microspheres significantly reduced both total and rate of gas production (FIG. 8). This indicates that the starch microspheres will not contribute to the uncomfortable pain and bloating experienced with some types of dietary fiber. Increasing the concentration of alginate used to create the microspheres beyond 1% reduced the total short chain fatty acids produced during 24 hrs of fermentation (Table 2); however, since the entrapment of starch in alginate appears to slow the rate of digestion and fermentation, it is likely that all samples would produce similar amounts of short chain fatty acids if the fermentation time were extended beyond 24 hr. Additionally, the proportion of butyrate produced increased when 2 or 3% alginate were used to prepare the microspheres (Table 2). This has specific applications for the delivery of higher amounts of butyrate to distal regions of the colon.

TABLE 2

| Sample | Acetate | Propionate | Butyrate |
|---|---|---|---|
| NCS | 59[a] | 18[a] | 23[b] |
| 1% | 61[a] | 15[b] | 24[b] |
| 2% | 55[b] | 13[c] | 32[a] |
| 3% | 53[b] | 15[b] | 32[a] |

Numbers in the same column with the same superscripts indicate no significant difference (p > 0.05).

Example 10

Targeting Different Areas of Small Intestine and Colon

Starch-containing microspheres of this invention can be targeted to selected areas of the small intestine and colon to provide energy (as glucose) and/or (fermentable fiber). Table 3 provides example formulations targeted to the numbered regions illustrated on FIG. 9.

TABLE 3

| No. | Starch/polymer/Co-polymer ratio | Crosslinker | Size (μ) |
|---|---|---|---|
| 1 | Normal corn starch:Alginate (40:1)<br>Normal corn starch:Gellan (20:1)<br>Waxy corn starch:Alginate (20:1) | 0.5-2% w/v<br>CaCl$_2$ | 50-100 |
| 2 | Normal corn starch:Alginate (20:1 to 10:1)<br>Normal corn starch:Alginate:Carageenan (10:1:0.5) | 0.5-2% w/v<br>CaCl$_2$ | 100-1000 |
| 3 | Normal corn starch:Alginate (10:1 to 5:1)<br>High amylose starch:Alginate (10:1 to 5:1) | 0.5-2% w/v<br>CaCl$_2$ | 100-1000 |
| 4 | Normal corn starch:Alginate (10:1 to 5:1)<br>Normal corn starch:Alginate:Chitosan (5:1:0.5)<br>High amylose starch:Alginate (10:1 to 5:1)<br>Corn fiber gum:Alginate (10:1) | 0.5-2% w/v<br>CaCl$_2$ | 500-2000 |
| 5 | Normal corn starch:Alginate (5:1 to 4:1)<br>Normal corn starch:Alginate:Chitosan (5:1:1.0)<br>High amylose starch:Alginate (5:1)<br>Corn fiber gum:Alginate (5:1)<br>Inulin:Alginate (5:1) | 0.5-2% w/v<br>CaCl$_2$ | 1500-2000 |

The type of polysaccharide, the type of copolymer, the relative amounts of polysaccharide/copolymer and starch, the type of starch, composition of starch and the size of the microspheres can be adjusted to improve targeting to selected regions as indicated. Additionally, the solubility properties of the copolymer and the addition of a polymer coating on the microparticles can be used to adjust targeting.

Table 3 also provides examples of microsphere delivery of fermentable fiber other than starch-based fiber. Corn fiber gum and inulin are fermentable fiber materials. Inulin in particular is a fermentable fiber that is considered to be a prebiotic material.

Example 11

Use of Polymer Coatings on Microparticles to Create Slowly Digestible Starches and Fibers Starch-entrapped microparticles using 1% alginate solution and native corn starch were prepared as in Example 1. The wet hydrogels were suspended in coating solutions including: 2% Hylon 5 [a high amylose (50%) starch that had been pressure cooked for 90 min]; 2% Hylon 7 [a high amylose (70%) starch that has been pressure cooked for 90 min]; 0.1% LMW (low molecular weight) Chitosan dissolved in 1% acetic acid; 0.1% MMW (medium molecular weight) Chitosan dissolved in 1% acetic acid; and 0.1% HMW (high molecular weight) Chitosan dissolved in 1% acetic acid. Starch digestibility profiles for coated microparticles are presented in FIG. 10. The coated particles can exhibit enhanced levels of SDS starch compared to uncoated materials.

Coated of the starch-containing microparticles and microspheres with solutions of polymers such as chitosan and high amylase starches can modify surface characteristics affecting enzyme accessibility and affecting digestion and/or fermentation rate of the starch in the microsphere.

The forgoing examples are illustrative and are in no way intended to limit the scope of the claims.

References

| U.S. Patent Documents | | |
|---|---|---|
| 2,517,595 | August 1950 | Owens et al. |
| 2,611,708 | September 1952 | Owens et al. |

-continued

| U.S. Patent Documents | | |
|---|---|---|
| 2,703,286 | March 1955 | Eppell |
| 4,192,900 | March 1980 | Cheng |
| 5,360,614 | November 1994 | Fox et al. |
| 5,545,410 | August 1996 | Fox et al. |
| 5,795,606 | August 1998 | Lapre et al. |
| 5,972,399 | October 1999 | Lapre et al. |
| 6,316,427 | November 2001 | Axelson et al. |
| 6,890,571 | May 2005 | Shi et al. |
| 6,929,817 | August 2005 | Shi et al. |
| 7,053,066 | May 2006 | Chawan |
| 0,127,453 | June 2006 | Harel |

| International Patent Documents | | |
|---|---|---|
| WO 2005044284 | May 2005 | Qi and Tester |
| WO 2005058973 | June 2005 | Muller et al. |
| WO 2004066955 | November 2005 | Han and Hamaker |

Other References

Eller et al., "Anaerobic roll tube media for nonselective enumeration and isolation of bacteria in human feces" (1971), Applied Microbiology, 22, 522-9.

Englyst et al.,"Classification and measurement of nutritionally important starch fractions", European Journal of Clinical Nutrition (1992) 46 (Suppl. 2), S33-S50.

Englyst et al., "Measurement of rapidly available glucose (RAG) in plant foods: a potential in vitro predictor of the glycemic response" (1996), British Journal of Nutrition, 75, 327-37.

FAO Food and Nutrition Paper 66, "Carbohydrates in human nutrition", Chapter 4-The Role of the Glycemic Index in Food Choice, pp. 25-30, Report from Apr. 14-18,1997.

Lebet et al., "Digestion procedure using mammalian enzymes to obtain substrates for in vitro fermentation studies" (1998), Lebensmittel Wissenschaft und Technologie 31, 509-15.

Obanni, M. and BeMiller, J. N.(1995) Identification of starch from various maize endosperm mutants via ghost structures. Cereal Chemistry 72:436-442 Playne, "Determination of ethanol, volatile fatty acids, lactic acid and succinic acids in fermentation liquids by gas chromatography" (1985), Journal of the Science of Food and Agriculture, 36, 638-44.

Wolevar et al., "Glycemic index methodology", Nutrition Research Reviews (2005) 18,145-171.

Wachters-Hagedoorn R E, Priebe M G, Heimweg J A J, Heiner A M, Englyst K N, Hoist J J, Stellaard F, Vonk R J. The Rate of Intestinal Glucose Absorption Is Correlated with Plasma Glucose-Dependent Insulinotropic Polypeptide Concentrations in Healthy Men. J Nutr 2006; 136: 1511-16.

We claim:

1. A method for preparation of a starch composition to provide fermentable fiber to regions of intestinal tract or colon in humans which method comprises mixing a composition consisting essentially of uncooked starch, and a solution of water and an ionically crosslinkable polymer to form a mixture; and forming crosslinked polymer matrix microparticles from the mixture, where each microparticle consists essentially of starch entrapped within the crosslinked polymer matrix, and where the uncooked starch in substantially all the microparticles is undigested and available for fermentation in colon, wherein the ionically crosslinkable polymer is alginate, pectin, gellan, carrageenan, chitosan or mixtures thereof.

2. The method of claim 1, wherein the microparticles contain about 75% or more by weight of starch.

3. The method of claim 1, wherein the weight ratio of ionically crosslinkable polymer to starch is about 0.01 to about 0.5 in the mixture.

4. The method of claim 1, wherein the concentration of alginate in the solution is about 1%.

5. The method of claim 4, wherein about 0.28 ml of gas per mg of starch is generated over about 24 hours when the starch in the microparticles is fermented in human fecal material at about 37 ° C.

6. The method of claim 5, wherein the rate at which gas is generated is between about 0.01 ml/mg starch per hour to about 0.02 ml/mg starch per hour.

7. The method of claim 1, wherein the concentration of alginate in the solution is about 2%.

8. The method of claim 7, wherein about 0.2 ml of gas per mg of starch is generated over about 24 hours when the starch in the microparticles is fermented in human fecal material at about 37 ° C.

9. The method of claim 8, wherein the rate at which gas is generated is about 0.008 ml/mg starch per hour.

10. The method of claim 1, wherein the concentration of alginate in the solution is about 3%.

11. The method of claim 10, wherein about 0.15 ml of gas per mg of starch is generated over about 24 hours when the starch in the microparticles is fermented in human fecal material at about 37 ° C.

12. The method of claim 11, wherein the rate at which gas is generated is about 0.006 ml/mg starch per hour.

13. The method of claim 1, wherein the concentration of alginate in the solution is between about 1% and about 3%.

14. The method of claim 13, wherein between about 0.15 ml and about 0.28 ml of gas per mg of starch is generated over about 24 hours when the starch in the microparticles is fermented in human fecal material at about 37 ° C.

15. The method of claim 13, wherein the rate at which gas is generated is between about 0.006 and about 0.02 ml/mg starch per hour.

16. The method of claim 13, wherein butyrate is produced between about 24/23 and about 32/23 times the amount of butyrate that is produced when an equivalent amount of normal cornstarch is fermented.

17. The method of claim 1, wherein the microparticles are between about 1 micron and about 5000 microns.

* * * * *